(12) United States Patent
Vlaskalic et al.

(10) Patent No.: US 11,406,311 B2
(45) Date of Patent: Aug. 9, 2022

(54) POCKET-SIZE FOLDING DEVICE WITH INTEGRATED ELECTRODES FOR RECORDING, PROCESSING AND TRANSMISSION WITH THREE ECG LEADS

(71) Applicant: HEARTPAL TECH DOO, Belgrade (RS)

(72) Inventors: Srdjan Vlaskalic, Belgrade (RS); Darko Boljevic, Belgrade (RS)

(73) Assignee: Heartpal Tech Doo, Belgrade (RS)

( * ) Notice: Subject to any disclaimer, the term of this patent is extended or adjusted under 35 U.S.C. 154(b) by 0 days.

(21) Appl. No.: 17/430,259

(22) PCT Filed: Nov. 14, 2019

(86) PCT No.: PCT/RS2019/000026
§ 371 (c)(1),
(2) Date: Aug. 11, 2021

(87) PCT Pub. No.: WO2020/167154
PCT Pub. Date: Aug. 20, 2020

(65) Prior Publication Data
US 2022/0039726 A1  Feb. 10, 2022

(30) Foreign Application Priority Data

Feb. 13, 2019 (RS) .................................. P-2019/0205

(51) Int. Cl.
*A61B 5/332* (2021.01)
*A61B 5/333* (2021.01)
(Continued)

(52) U.S. Cl.
CPC .............. *A61B 5/333* (2021.01); *A61B 5/002* (2013.01); *A61B 5/0006* (2013.01); *A61B 5/282* (2021.01);
(Continued)

(58) Field of Classification Search
CPC ....... A61B 5/333; A61B 5/0006; A61B 5/002; A61B 5/282; A61B 5/332; A61B 5/6823; A61B 5/6826
See application file for complete search history.

(56) References Cited

U.S. PATENT DOCUMENTS 5,339,823 A * 8/1994 Reinhold, Jr. ......... A61B 5/282
600/523
5,505,202 A * 4/1996 Mogi .................... A61B 5/282
600/390

(Continued)

FOREIGN PATENT DOCUMENTS

| CN | 208287000 U | 12/2018 | |
| EP | 0657136 A1 | 6/1995 | |
| WO | WO-2020232040 A1 * | 11/2020 | ............. A61B 5/361 |

*Primary Examiner* — Eugene T Wu
(74) *Attorney, Agent, or Firm* — The Watson IP Group, PLC; Jovan N. Jovanovic

(57) ABSTRACT

Pocket-size folding device with integrated electrodes for recording, processing and transmission with three ECG leads is a hand held ECG device with integrated electrodes used to measure, process and transmit three ECG leads to the remote diagnostic center. When in closed position and not in use the device is more compact and robust so it can be carried in a pocket or a pouch while electrodes are protected from getting dirty or damaged When opening it into a measuring position it becomes ergonomic. It is well adapted to the shape of a user's chest which ensures stable and reliable contact between chest electrodes (4-6) and chest surface. Finger electrodes (7,8) are designed for a contact with left hand and right hand thumbs as well as supporting the device and ensuring sufficient pressure to the chest without intense use of user's arms. The device is compact, it doesn't use cables or levers which makes it very easy to use.

6 Claims, 1 Drawing Sheet

(51) Int. Cl.
*A61B 5/282* (2021.01)
*A61B 5/00* (2006.01)

(52) U.S. Cl.
CPC ............ *A61B 5/332* (2021.01); *A61B 5/6823* (2013.01); *A61B 5/6826* (2013.01)

(56) References Cited

U.S. PATENT DOCUMENTS

| | | | | |
|---|---|---|---|---|
| 6,486,779 | B1* | 11/2002 | Alroy | A61B 5/0006 340/568.7 |
| 8,594,771 | B2 | 11/2013 | Kohls et al. | |
| 2003/0187363 | A1* | 10/2003 | Alroy | A61B 5/0006 600/509 |
| 2014/0163349 | A1* | 6/2014 | Amitai | A61B 5/6826 600/393 |
| 2016/0296132 | A1* | 10/2016 | Bojovic | G16H 40/67 |

* cited by examiner

US 11,406,311 B2

POCKET-SIZE FOLDING DEVICE WITH INTEGRATED ELECTRODES FOR RECORDING, PROCESSING AND TRANSMISSION WITH THREE ECG LEADS

TECHNICAL FIELD

The present invention relates to the field of electronics for recording, processing and transmission of electrocardiograph (ECG) signals via a commercial telecommunication network. More particularly, the invention concerns a portable hand held device with integrated electrodes for recording 3 ECG leads from the human surface.

BACKGROUND ART

Technical Problem

Technical issue being solved by the present invention consists of constructional upgrade of a portable pocket-size device for recording, processing and transmission of three ECG signals as described in patent document EP1659936 A1, (Bojovic et al.) 2003. The aim was to reduce device dimensions, decrease height of the chest electrodes and protect them from grime and damage when the device is not used. Above mentioned modification should preserve the distance between active chest electrodes, enable good and stable contact of chest electrodes with chest area near pectoralis muscle and electrodes which are connected to left and right hand fingers in order to obtain good quality of recorded ECG signals

State of the Art

Mobile portable ECG devices with integrated electrodes for recording three or more ECG leads used for urgent cardiac diagnostics are known from the prior art. User of such devices can record his/her ECG wherever they are and send it to a remote diagnostic centre via a commercial network.

Description of a mobile pocket-size device with integrated electrodes for recording three ECG leads which are sent to a remote diagnostic centre and are presented to a cardiologist as 12 reconstructed ECG leads is given in a patent document EP1659936 A1, (Bojovic 2003). The device is designed with two integrated electrodes placed on one side of the device. They can be reached with left hand and right hand fingers. Two electrodes placed on the opposite side are connected to the patient's chest. In addition to the active chest electrodes, there is another, third electrode, which serves as common grounding and it ensures stability of the device by having it rested on three points of the chest. This embodiment assumes that chest electrodes need to be 100-120 mm apart and sufficiently high (around 8-10 mm) in order to accommodate for patient's morphology (chest area curvature). Such shape should avoid contact and leaning of device casing on the patient's chest with as it would affect device stability as well as chest electrodes contact. Aforementioned constraints limit any further reduction of the mobile device dimensions.

Also, all electrodes are exposed at all the time so they could get dirty or damaged when carried around and storing the device when not used. In particular, this is very important when the contact area is in pyramidal shape (Khannaet al., Skin penetration and fracture strength testing of silicon dioxide microneedles, Sensors and Actuators A 170 (2011) 180-186), or they have a layer of contact material like silver/silver-chloride or similar (Weder et al. Embroidered Electrode with Silver/Titanium Coating for Long-Term ECG Monitoring, Sensors 2015, 15, 1750-1759).

In a patent document U.S. Pat. No. 6,363,274, Scalisi et al. describes a hand held pocket size device with foldable electrodes. The device is recording five ECG leads directly and reconstructs additional three channels. This device has two electrodes for left hand and right hand thumbs and three electrodes to be applied on the patient's thorax, as well as a skin electrode for acquiring a third peripheral signal, connected to the housing by a connecting cable. This design enables further reduction of the device size by utilising foldable levers, retractable rod and a cable.

In a patent document US20100174204, Danteny discloses hand held ECG device which can record 12 ECG channels directly. It can store them in memory and transfer them to the remote diagnostic centre. The device has a concave surface that can be adapted to the patient's morphology as well as ensure good electric contact of chest electrodes. The casing is provided with six integrated chest electrodes, two finger electrodes (left and right hand) disposed at two foldable arms pivotally connected to the casing, as well as one peripheral electrode, attached to the casing by a cable.

Hand-held devices mentioned above enable recording of three or more ECG leads, their processing and transmission to a remote diagnostic centre. However, they are relatively big to be carried around in a pocket or a pouch and complicated to handle since they involve using cables and un-protected electrodes. Therefore, there is a need for a hand held ECG device that will have performances of aforementioned devices and, at the same time, is compact and without additional parts like cables and rods. It should be used in a simple and reliable manner, be small and robust, so that it can be comfortably carried around in a pocket or a pouch, and in such a way that the electrodes are protected from getting dirty or being damaged.

DISCLOSURE OF INVENTION

The object of this invention is to overcome the above-mentioned drawbacks and constraints of existing pocket size ECG devices and provide compact three-channel hand held ECG device with no additional parts like cables and rods. It should be simple and reliable to use, ergonomical and adaptable to the morphology of a patient's chest, small in size and robust so that it can be carried around in a pocket or a pouch while ensuring that electrodes are protected from getting dirty or being damaged.

To meet these requirements, a hand-held folding three-lead ECG device has been designed. Users can use that device to record their own ECG. This device represents the improved version of a hand-held three-lead ECG device with integrated electrodes as described in a patent document EP1659936 A1, (Bojovic 2003).

Device casing consists of an upper and rear face connected by a pivot. For recording position, the device is placed on the patient's chest in such way that the upper face is pointed towards the head and rear face towards the legs. At the device inner side, facing the patient's body while recording, there are two active measuring electrodes mounted as well as the third, ground electrode. An active chest electrode and the ground electrode are mounted at the upper casing—the one closer to the user's head, near the edge and opposite side from the pivot connection. By doing so, when in operational position, the device is resting on the chest at three points. That ensures mechanical stability as well as stable electrical contact with a skin. In another embodiment, the ground electrode may be mounted on the lower casing, keeping resting on the chest at three points.

Electrodes for the contact with left hand and right hand fingers are placed on or near the edges side of the device on the upper part of the casing. Finger contact electrodes have two purposes: ensuring electric contacts with left and right hand fingers as well as supporting the device during recording. When in recording position the upper side of the casing (where the finger electrodes are placed) is oriented towards the user's head. which ensures that supporting of the device and pressure of the electrodes against the chest is achieved in most relaxing hands position. That position reduces disturbances induced by hand muscles activity.

The upper and rear face of the device can rotate around the pivot joining them. The pivot is designed in such a way that the angle between the upper and rear part of the casing can vary between 0 and around 150 degrees. In the open position used for recording, the angle between parts of the casing is restricted to around 150 degrees so that the distance between active chest electrodes is 100-120 mm. By doing so, the device in the recording position becomes ergonomic as it adjusts to the users body morphology of the chest area. Thus any contact between the casing and the body surface is prevented which results in good and stable electric contact of chest electrodes and skin. This is particularly important for male users with a large chest muscle (pectoralis major).

In folded position (used for storing or carrying the device in a pocket or a pouch). the angle between the parts is 0 degrees so that both parts lay on top of each other. That reduces the length of the device significantly and protects the electrodes from getting dirty or damaged. In this way. the folded device becomes compact and handy to store or carry in a pocket or a pouch.

The upper side of the casing contains finger electrodes on the outer side. One active chest electrode is on the inner side as well as a common ground electrode. This is where an electronic module is situated, too. It performs recording, storing and transmission to the remote diagnostic centre functions. It also enables communication with a smart phone which contains an application program used by a user to activate, monitor and control the recording process.

When the device is in open position the rear side of the casing is used as a support for a chest electrode. That electrode is connected to the electronic module situated in the upper part of the casing. The rear part of the casing serves as a cover for the chest electrodes once the device is in closed position.

BRIEF DESCRIPTION OF THE DRAWINGS

The invention is described in detail on the implemented example shown below.

BEST MODE FOR CARRYING OUT OF THE INVENTION

Figure 1:
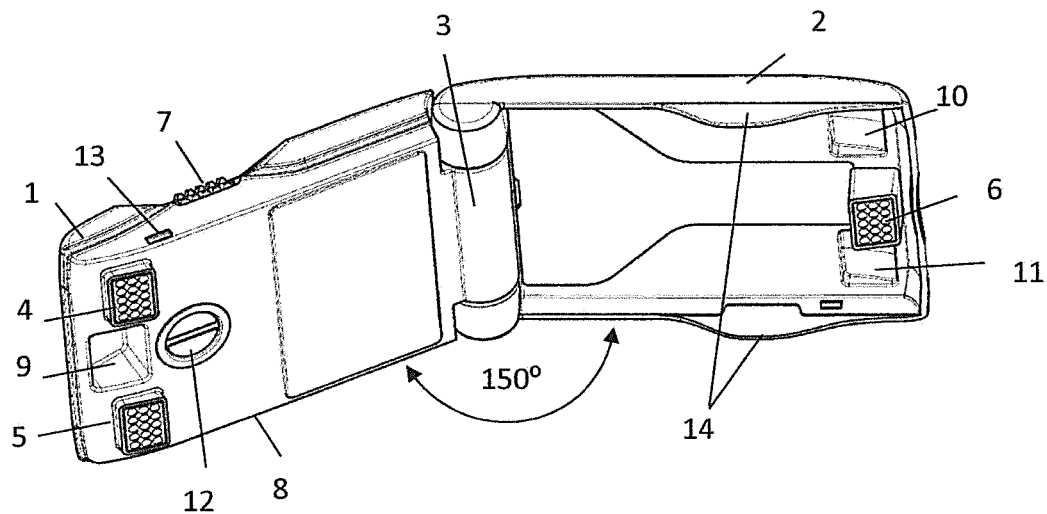
FIG. 1 Simplified drawing of a folding device with integrated electrodes for recording, processing and transmission of three special ECG leads in an open measuring position FIG. 2 Simplified drawing of axonometric view of the device with integrated electrodes for recording, processing and transmission of three special ECG leads in a closed position—a cross section through a chest electrode.
Figure 2:
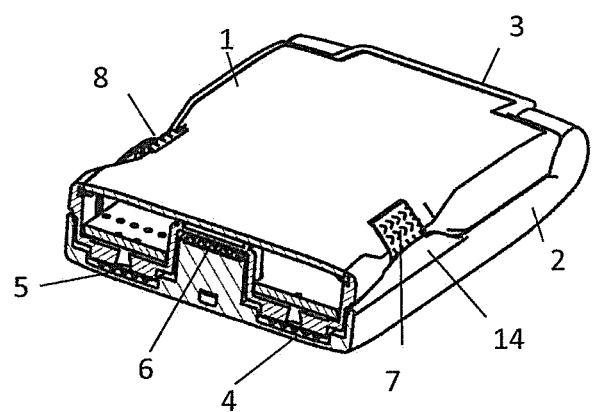

The example of the embodiment is shown on FIG. 1 and FIG. 2. Folding device with integrated electrodes for recording, processing and transmission of three special ECG leads consists of an upper casing part 1 and rear casing part 2 which are joined by a pivot 3. The inner side of the upper casing 1 is facing the patient's chest and contains an active measuring electrode 4 and electrode 5 which acts as a common ground. Between them is a recess 9 used to place an active electrode 6 when device casing is in closed position. An on/off switch 12 is mounted on the same side of the device.

Electrode 7 is placed on the upper part of the casing. That electrode is used for a contact with a right hand thumb. The electrode is indented into casing edge in such a way that the plane containing the electrode forms an angle of approximately 45 degrees with the plane containing front of the upper part of the casing. Electrode 8 is placed at the opposite side of the upper edge of the casing and is used to contact left hand thumb. Finger electrodes placed in such a way enable supporting force of both thumbs (placed on electrodes 7 and 8) transfer towards the user's body. That ensures an additional pressure on the chest electrodes 4, 5 and 6 and helps forming a stable electric connection with the user's chest surface.

An USB connector 13 is mounted on one of the casing side edges. It is used for recharging of an accumulating battery placed inside casing upper part.

Rear part of the casing 2 is shaped as a lid which covers the upper part of the casing when closed. An active measuring chest electrode 6 is mounted on it. That electrode is connected by a wire with an electronic device placed inside the upper side of the device casing. There are two recesses 10 and 11 on both sides of the electrode 6. When device is in closed position electrode 6 gets into recess 9. Electrodes 4 and 5 are placed in recess 10 and 11 respectively. This allows grip between rear casing part 2 and upper casing part 1. The edges 14 of the lower casing part are wider at the side opposite from the pivot. The purpose of those is to protect finger electrodes 7 and 8 from getting dirty or damaged.

Pivot mechanism 3 joins front and rear part of the casing. It has been designed in such a way that an angle between the upper and rear part of the casing can vary between 0 and about 150 degrees. In the open position used for recording, the angle between parts of the casing is restricted to about 150 degrees so that the distance between active chest electrodes is about 100 mm. Pivotal mechanism contains a spring which produces enough force to make device mechanically stable in both open and closed position. At the same time a user can easily open or fold the device. By doing so, the device in the recording position becomes ergonomic as it adjusts to the user's body morphology of the chest area. Thus any contact between the casing and the body surface is prevented which results in good and stable electric contact of chest electrodes and skin.

In folded position (used for storing or carrying the device in a pocket or a pouch) the angle between the parts is 0 degrees so that both parts lay on top of each other. In this position rear part of the casing 2 has a function of a lid which covers front part of the casing 1 and protects the chest electrodes 4, 5 and 6 as well as the switch 12 from getting dirty or damaged. In addition, widenings 14 at the rear part of the casing protect electrodes 7 and 8. In this way, the folded device becomes compact and handy to store or carry in a pocket or a pouch. This implementation has following approximate dimensions: length 80 mm, width 50 mm and thickness 9 mm.

Chest electrodes 4, 5 and 6 are around 2 mm higher than inner surface of the front and rear parts of the casing surfaces. The recess 9 is also 2 mm deep, which allows placement of the electrode 6 when the device is in closed position. Length of chest electrodes is about 15 mm and width is about 10 mm. Surface of the chest electrodes is modelled in such a way that it has three rows with three conic bulges in each row. Finger electrodes 7 and 8 are about 15 mm long and about 5 mm wide. They have two rows with five conic bulges in each row.

Both electronic module and a charge battery are placed in the upper part of the casing. The electronic module performs the following functions: recording, storing and transmission to the remote diagnostic using a commercial telecommunication network. It also enables communication with a smart phone using built-in Bluetooth component and it's aerial. Smart phone contains an application program used by a user to activate, monitor and control the recording process.

Electric connection between electrodes and the electronic module is implemented as described in the patent document EP1659936 A1, (Bojovic 2003). More precisely, signals are measured against the electrode contacted by right hand fingers. Three signals are being measured which represent a potential difference between: a) electrode 8 and electrode 7, b) electrode 4 and electrode 7 and c) electrode 6 and electrode 7. Active electrodes are connected inside the electronic module in the following way: electrodes 8 and 7 connected to the first amplifier input, electrodes 4 and 7 to the second amplifier input and electrodes 6 and 7 to the third amplifier input. Amplified signals are digitized and transmitted to the smart phone using the Bluetooth connection and further on over the commercial communication network to the remote diagnostic center.

The essence of the invention will not change if the ground electrode is mounted at the rear part of the casing next to the chest electrode 6 or some other place. Also, electronic module can be placed in the rear part of the casing while the upper part of the casing acts as a lid.

INDUSTRIAL APPLICABILITY

Folding device with integrated electrodes, which records, processes and transmits three ECG leads can be used for an urgent cardiac diagnostics in the following way. A user can record his/her own ECG at any given location and send it to a remote cardiac centre via commercial communication network. That is where a doctor on duty receives reconstructed standard 12 lead ECG. The doctor on duty will be able to verify existence of an urgent cardiac condition like an acute myocardial infraction. In that case, he will get in touch with the patient and help him/her to be taken care of. In addition, other pathological cardiac conditions can be discovered or monitored and appropriate home or hospital care can be provided.

The invention claimed is:

1. A foldable mobile three-lead cardiac monitoring device for recording, processing and transmitting three ECG leads comprising:
   a casing with two parts connected by a pivotal joint;
   first chest electrode placed on the inner side of the first part of the casing;
   second chest electrode placed on the inner side of the second part of the casing; and
   two finger electrodes mounted on the outer sides of the first part of the casing to enable contact with left and right hand fingers.

2. The device according to claim 1, where first and second parts of the casing are approximately parallel when in a closed position, and create an angle of 150 degrees approximately when in a fully opened position.

3. The device according to claim 1, where the first and second chest electrodes are around 100 mm apart when in a fully opened position.

4. The device according to claim 1, where an integrated chest electrode placed on the inner side on one of the parts of the casing is configured as a common ground.

5. The device according to claim 1, where the two finger electrodes for contacting left and right hand fingers of a patient are mounted on the side edges of the outer part of the first part of the casing.

6. The device according to claim 5, where contact surfaces of the two finger electrodes are forming an angle of about 45 degrees against the surface of the outer side of the first part of the device casing.

* * * * *